(12) United States Patent
Basha et al.

(10) Patent No.: US 6,376,488 B1
(45) Date of Patent: Apr. 23, 2002

(54) BENZOXAZINE α-1 ADRENERGIC COMPOUNDS

(75) Inventors: Fatima Z. Basha, Lake Forest; Michael D. Wendt, Vernon Hills, both of IL (US); John K. Pratt, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/657,296

(22) Filed: Sep. 7, 2000

(51) Int. Cl.$^7$ .................. A61K 31/5365; C07D 405/14
(52) U.S. Cl. ..................... 514/230.2; 544/101
(58) Field of Search ..................... 544/101; 514/230.2

(56) References Cited

FOREIGN PATENT DOCUMENTS

WO    WO-00/05230    *    2/2000

OTHER PUBLICATIONS

Gazis et al Can. J. Physiol. Pharmacol. 67 (1989) 1586–1590 (Medline abstract only).*
Ibuki et al Biol. Reprod. 56 (1997) 632–639.*
M. Caine, et al., Brit. J. Urol., 47:193–202 (1975).
T. Thien, K.P. Delacre, F. M. J. Debruyne, R. A. P. Koene, Br. Med. Journal, 622–623 (1978).
C. R. Chapple, M. L. Aubry, S. James, M. Greengrass, G. Burnstock, R. T. Turner–Warwick, Br. J. Urol. 63: 487–496 (1989).
R. A. Janknegt, C. R. Chapple, Eur. Urol. 24:319–326 (1993).
H. Lepor, G. Knapp–Maloney, J. Urol. 145:263A (1991).
W. Chow, D. Hahn, D. Sandhu, Br. J. Urol. 65: 36–38 (1990).
C. R. Chapple, T. J. Christmas, E. J. G. Milroy, Urol. Int. 45: 47–55 (1990).
Lepor, H., Alpha Blockade for the Treatment of Benign Prostatic Hyperplasia, Urol. Clin. N. Amer., 22: 375–386, 1995.
Rosier, P.F.W.M., J.J.M.C.H, de la Rosette, H. Wijkstra, Ph.E.V. Van Kerrebroeck and F.M.J. Debruyne, Is Detrusor Instability in Elder Males Related to the Grade of Obstruction?, Neurourol. Urodynam., 14:625–633, 1995.
Andersson, K–E., Prostatic and Extraprostatic αadrenoceptors Contributions to the Lower Urinary Tract Symptoms in Benign Prostatic Hyperplasia, Scand. J. Urol. And Nephrol., 30: 105–111, 1996.
Gittes, R. F. and R. M. Nakamura, Female urethral syndrome: A female prostatis?, Western J. Medicine, 164: 435–438, 1996.
Miller and Marshall, Uterine Response to Nerve Stimulation: Relation to Hormonal Status and Catecholamines, Am. J. Physiol., 302: 859–863, 1965.
Hoffman, B B., T. N. Lavin, R.J. Lefkowitz and R. R. Ruffolo, Jr., Alpha Adrenergic Receptor Subtypes in Rabbit Uterus: Mediation of Myometrial Concentration and Regulation by Estrogens, J. Pharmacol. Exp. Ther., 219: 290–295, 1981.
A. Goldfein, Regulation of Myometrial Andrenoreceptors and Adrenergic Response by Sex Steroids, Mol. Pharmacol., 20: 52–58, 1981.
Gupta et al., Indian Journal of Chemistry 13, 462–467 (1975).
Petrov & Stephenson, Journal of Pharmacology, 5, (1953) pp 359–369.
Muehlman, F.L. and Day, A.R., JACS 78 (1956) 242.
Chem. Abstr., 56 (1962) 871 1h.
Beck, JOC 37 (1972) 3224.
Norman, M.H. et. Al., J.Med.Chem., (1996) 4692–4703.
Dunn, A.D. Norrie, R., J.Het.Chem., 24 (1987) 85–89.
Journal of Heterocyclic Chemistry, 24: 85 (1987).
Greengrass and Bremner (Eur. J. Pharmacol. 55: 323–326 (1979).
Hancock, A.A., Kyncl, J.J., Martin, Y.C. and Debernardis, J.F., Receptor Res. 8 23–46 (1988).
Prescott, Ed., Methods in Cell Biology, vol. XIV, Academic Press, New York, N.Y., (1976), p 33 et seq.
Roberts, J.M., P.A. Insel and A. Goldfein, Regulation of Myometrial Adrenoreceptors and Adrenergic Response by Sex Steroids, Mol. Pharmacol., 20: 52 –58, 1981.
S. M. Berge et al, J. Pharmaceutical Sciences, 1977, 66: 1 et seq.

* cited by examiner

*Primary Examiner*—John M. Ford
(74) *Attorney, Agent, or Firm*—Michael J. Ward

(57) ABSTRACT

The present invention relates to compounds having formula I

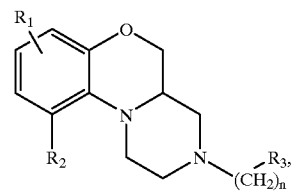

and to pharmaceutically acceptable salts thereof. Compounds of formula I inhibit $\alpha_1$ adrenoreceptors and may be useful for treating benign prostatic hyperplasia (also called benign prostatic hypertrophy) and other urological diseases such as bladder outlet obstruction, neurogenic bladder and gynecological syndromes.

13 Claims, No Drawings

BENZOXAZINE α-1 ADRENERGIC COMPOUNDS

TECHNICAL FIELD

The present invention relates to novel organic compounds and compositions which are $\alpha_1$ adrenoreceptor antagonists, a method for inhibiting $\alpha_1$ adrenoreceptors and a method for treating benign prostatic hyperplasia (BPH), bladder outlet obstruction (BOO), neurogenic bladder, and gynecological syndromes such as dysmenorrhea (benign prostatic hypertrophy).

BACKGROUND OF THE INVENTION

Adrenergic neurons play a major role in the innervation of heart, blood vessel and smooth muscle tissue. Compounds capable of interacting with adrenoreceptor sites within adrenergic nerves can initiate physiological responses including vasoconstriction, vasodilation and increased or decreased heart rate (chronotropic), contractility (inotropic) and metabolic activity. Adrenergic compounds have been employed to affect these and other physiological responses, however, many adrenergic compounds do not possess significant selectivity to enable desirable interactions with adrenergic adrenoreceptor sites. That is, these adrenergic compounds do not demonstrate a high degree of specificity for differing adrenoreceptor types within adrenergic neurons in order to obtain a desired physiological response separate from other possible, and perhaps less desirable, responses of the system under treatment.

Benign prostatic hyperplasia (BPH) is a condition which develops in middle-aged and elderly males and refers to the benign overgrowth of the stromal and epithelial elements of the prostate associated with aging. Symptoms of BPH include increased frequency of urination, nocturia, a weak urine stream and hesitancy or delay in starting the urine flow. Chronic consequences of BPH can include hypertrophy of bladder smooth muscle, a decompensated bladder and an increased incidence of urinary tract infection.

Typically, BPH begins at an age in the mid-fifties and is the most common cause of urinary tract problems of men of this age. BPH is apparently rare in men prior to age 40, but at age 60, approximately 50% of men have histological evidence of BPH. The prevalence of BPH continues to increase with age until, at age 80, approximately 80% of men have pathological evidence of BPH.

Although prostatic hyperplasia is a common finding in older men, the presence of urinary symptoms is the essential feature that distinguishes simple anatomic enlargement of the prostate from prostatism, which is the clinical syndrome whereby the patient experiences significant obstruction of urinary flow. It is not uncommon in older men to have a palpably enlarged prostate without showing the symptoms of prostatism. From the patient's perspective, however, the incidence and progression of urinary symptoms are more important than the mere presence of an enlarged prostate.

The discovery of large numbers of alpha-adrenergic adrenoreceptors in the smooth muscle of the prostatic capsule and bladder neck led to the conclusion that there is both a static and a dynamic component to bladder outlet obstruction associated with BPH (M. Caine, et al., Brit. J. Urol., 47: 193–202 (1975)). The static component derives from progressive hyperplasia of the aging prostate and leads to urethral narrowing with symptoms of urinary obstruction. Superimposed on this essentially mechanical problem is the variable degree of smooth muscle contraction controlled by the sympatheic nervous system which is affected by factors such as stress, cold and sympathomimetic drugs. It is this dynamic component which explains the often rapid fluctuations in symptoms observed in patients with prostatism.

The currently most effective treatment for BPH is surgical transurethral resection of the prostate (TURP). Since it removes the obstructing tissue (C. Chapple, Br. Med. Journal 304: 1198–1199 (1992)), it is a treatment which is directed to the static and dynamic components of BPH. However, this surgical treatment is associated with rates of mortality (1%) and adverse events (incontinence (2–4%), infection (5–10%), and impotence (5–10%)). A non-invasive alternative treatment would therefore be highly desirable.

The incidental clinical observation that urinary incontinence developed in women during antihypertensive treatment with prazosin (T. Thien, K. P. Delacre, F. M. J. Debruyne, R. A. P. Koene, Br. Med. Journal, 622–623 (1978)) and the experimental work of Caine (op cit.) contributed to the recognition of the potential role of selective a, adrenoreceptor blockade in diseases of the lower urinary tract. Subsequent studies by several groups have documented the functional role of $\alpha_1$ adrenoreceptors relative to $\alpha_2$ adrenoreceptors in the stromal compartment of the prostate, thereby providing a putative molecular basis for the use of specific $\alpha_1$ adrenoreceptor blockers in the non-surgical management of BPH (C. R. Chapple, M. L. Aubry, S. James, M. Greengrass, G. Burnstock, R. T. Turner-Warwick, Br. J. Urol. 63: 487–496 (1989)). Clinical efficacy of $\alpha_1$ antagonists in BPH has been demonstrated with several non-selective $\alpha_1$ blockers, including terazosin (Hytrin®), prazosin, and doxazosin. Treatment periods as short as two to four weeks with $\alpha_1$ adrenoreceptor blockers have shown objective improvements in the mean and maximum urinary flow rates (14–96%) with subjective improvements in patients'symptom scores (R. A. Janknegt, C. R. Chapple, Eur. Urol. 24: 319–326 (1993)). Longer term studies with terazosin, indoramin, prazosin and doxazosin have similarly demonstrated significant improvements in urinary flow rates and subjective symptom scores (R. A. Janknegt, op. cit., H. Lepor, G. Knapp-Maloney, J. Urol. 145: 263A (1991), W. Chow, D. Hahn, D. Sandhu, Br. J. Urol. 65: 36–38 (1990) and C. R. Chapple, T. J. Christmas, E. J. G. Milroy, Urol. Int. 45: 47–55 (1990)). However, these agents possess similar dose-limiting side effects including hypotension, dizziness and muscle fatigue.

In recent years, it has become clear that BPH and bladder outlet obstruction (BOO) are clinically differentiable, and that the severity of clinical BPH is related to many factors in addition to BOO (Lepor, H., Alpha Blockade for the Treatment of Benign Prostatic Hyperplasia, Urol. Clin. N. Amer., 22: 375–386, 1995.). For example, BOO may be related to other urological symptoms such as detrusor instability (Rosier, P. F. W. M., J. J. M. C. H. de la Rosette, H. Wijkstra, Ph.E. V. Van Kerrebroeck and F. M. J. Debruyne, Is Detrusor Instability in Elderly Males Related to the Grade of Obstruction?, Neurourol. Urodynam., 14: 625–633, 1995). Additionally, the role of extraprostatic $\alpha_1$ adrenoreceptors has been postulated as important in the etiology of lower urinary tract symptoms, such that antagonism of these receptors in spinal cord, ganglia, nerve terminals, bladder and bladder neck or the external urethral sphincter could be important in pharmacotherapy of urological conditions such as BOO or neurogenic bladder (Andersson, K-E., Prostatic and Extraprostatic a adrenoceptors Contributions to the Lower Urinary Tract Symptoms in Benign Prostatic Hyperplasia, Scand. J. Urol. and Nephrol., 30: 105–111, 1996). The recognition that women possess paraurethral glands which have anatomical, histological and biochemical similarities to the male prostate (Gittes, R. F. and R. M. Nakamura, Female urethral syndrome: A female prostatitis?, Western J. Medicine, 164: 435–438, 1996) suggests a potential role for $\alpha_1$ adrenoreceptor antagonist pharmacotherapy for amelioration of some symptoms of female urethral syndromes. In addition, α adrenoreceptors are functionally important to smooth muscle contraction in the uterus (Miller, M. D. and J. M. Marshall, Uterine Response to Nerve Stimulation: Relation to Hormonal Status and Catecholamines, Am. J. Physiol., 209: 859–863, 1965) and the modulation of sympathetic responses to catecholamines is enhanced by elevations in the levels of estrogens (Miller and Marshall, Uterine Response to Nerve Stimulation: Relation to Hormonal Status and Catecholamines, Am. J. Physiol., 209: 859–863, 1965). Consistent with this observation are data showing increasing levels of α adrenoreceptor responses and receptor density following estrogen administration to animals (Hoffman, B. B., T. N. Lavin, R. J. Lefkowitz and R. R. Ruffolo, Jr., *Alpha-Adrenergic Receptor Subtypes in Rabbit Uterus: Mediation of Myometrial Contraction and Regulation by Estrogens*, J. Pharmacol. Exp. Ther., 219: 290–295, 1981, and Roberts, J. M., P. A. Insel and A. Goldfein, Regulation of Myometrial Adrenoreceptors and Adrenergic Response by Sex Steroids, Mol. Pharmacol., 20: 52–58, 1981). Thus, hormonal regulation of $\alpha_1$ adrenoreceptor sensitivity could play a role in enhanced uterine contractions in dysmenorrhea, a condition for which selective $\alpha_1$ adrenoreceptor antagonists could have therapeutic potential. Therefore, there exists a need for a "uro-selective" $\alpha_1$ antagonist with reduced side effect liabilities.

SUMMARY OF THE INVENTION

In its principle embodiment, the present invention provides compounds of formula I

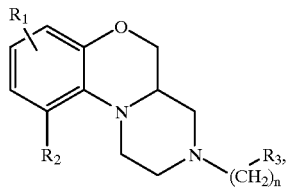

or a pharmaceutically acceptable salt thereof, wherein n is an integer of 2–4;

$R_1$ and $R_2$ are independently selected from hydrogen, alkenyl, alkoxy, alkoxyalkyl, alkoxycarbonyl, alkyl, alkynyl, amino, aminoalkyl, carboxy, carboxyalkyl, halogen, hydroxy, hydroxyalkyl, and nitro; and $R_3$ is selected from

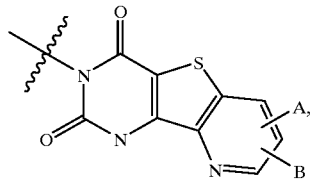

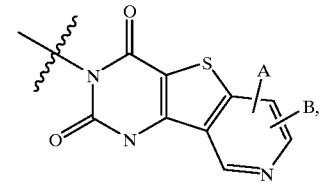

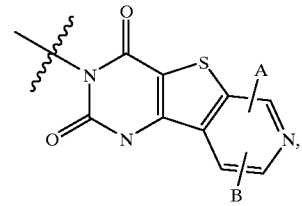

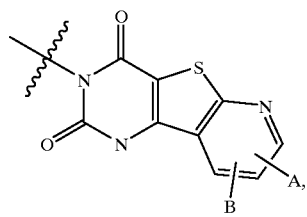

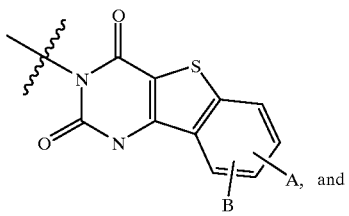

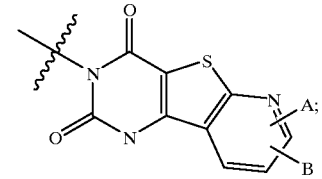

wherein A and B are independently selected from alkoxy, alkoxycarbonyl, alkyl, carboxy, cyano, halogen, hydroxyalkyl, nitro, and phenyl.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment, the present invention provides compounds of formula I

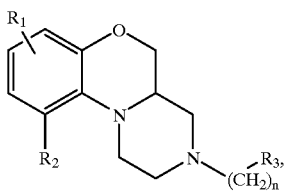

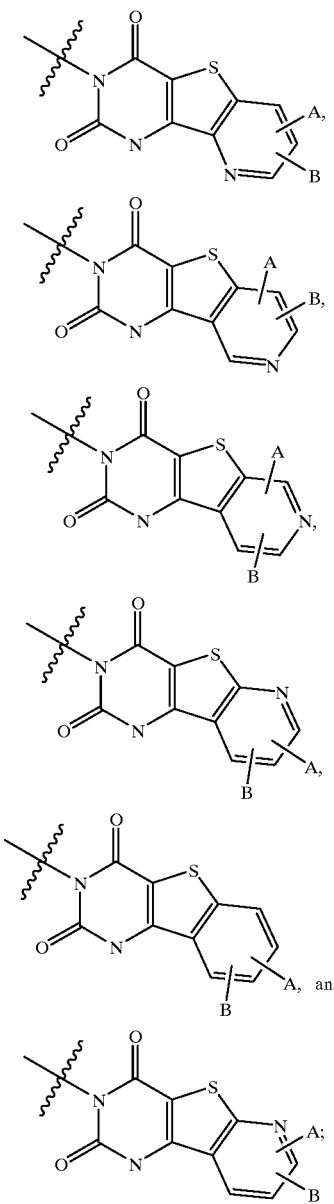

or a pharmaceutically acceptable salt thereof, wherein n is an integer of 2–4;

$R_1$ and $R_2$ are independently selected from hydrogen, alkenyl, alkoxy, alkoxyalkyl, alkoxycarbonyl, alkyl, alkynyl, amino, aminoalkyl, carboxy, carboxyalkyl, halogen, hydroxy, hydroxyalkyl, and nitro; and $R_3$ is selected from the group consisting of wherein A and B are independently selected from alkoxy, alkoxycarbonyl, alkyl, carboxy, cyano, halogen, hydroxyalkyl, nitro, and phenyl.

In a preferred embodiment, compounds of the present invention have formula 11

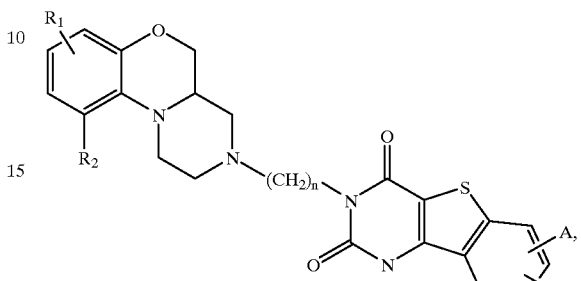

or a pharmaceutically acceptable salt thereof wherein $R_1$, $R_2$, A, B, and n are as defined in formula I.

In another preferred embodiment, compounds of the present invention have formula III

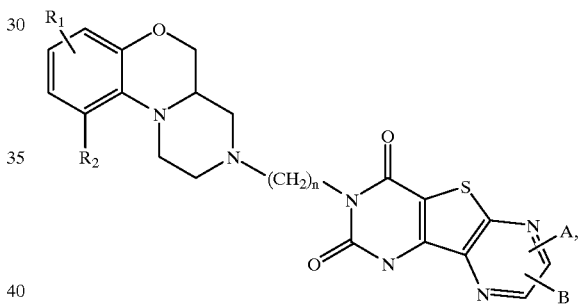

or a pharmaceutically acceptable salt thereof wherein $R_1$, $R_2$, A, B, and n are as defined in formula I.

In another preferred embodiment, compounds of the present invention have formula IV

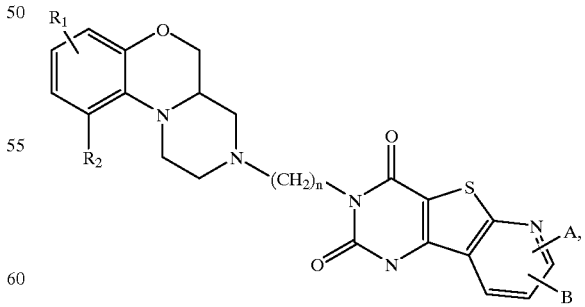

or a pharmaceutically acceptable salt thereof wherein $R_1$, $R_2$, A, B, and n are as defined in formula I.

In another preferred embodiment, compounds of the present invention have formula V

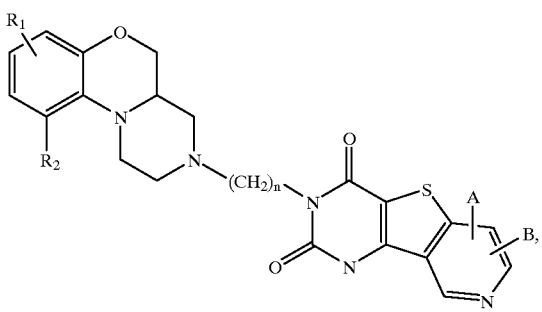

V or a pharmaceutically acceptable salt thereof wherein $R_1$, $R_2$, A, B, and n are as defined in formula 1.

In another preferred embodiment, compounds of the present invention have formula VI

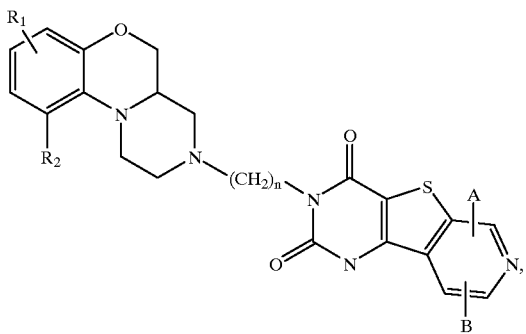

VI or a pharmaceutically acceptable salt thereof wherein $R_1$, $R_2$, A, B, and n are as defined in formula I.

In another preferred embodiment, compounds of the present invention have formula VII

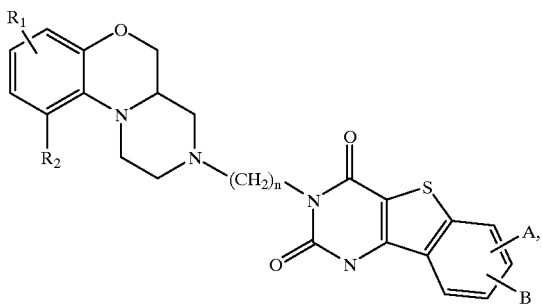

VII or a pharmaceutically acceptable salt thereof wherein $R_1$, $R_2$, A, B, and n are as defined in formula I.

In another preferred embodiment, the present invention relates to pharmaceutical compositions which comprise a therapeutically effective amount of a compound of formula I–VII in combination with a pharmaceutically effective carrier.

In another preferred embodiment, the present invention relates to a method of antagonizing alpha-1 adrenoreceptors in a host mammal, particularly humans, by administering a therapeutically effective amount of a composition comprising a compound of formula I–VII.

In another preferred embodiment, the present invention relates to a method of treating benign prostatic hyperplasia in a mammal, particularly humans, by administering to a mammal an effective amount of a compound of formula I–VII.

In another preferred embodiment, the present invention relates to a method of treating bladder outlet obstruction in a host mammal, in particular humans, in need of such treatment by administering a therapeutically effective amount of a compound of formula I–VII.

In another preferred embodiment, the invention relates to a method of treating neurogenic bladder in a host mammal, in particular humans, in need of such treatment by administering a therapeutically effective amount of a compound of formula I–VII.

In another preferred embodiment, the invention relates to a method of treating uterine smooth muscle contraction in a female host mammal, in particular humans, in need of such treatment by administering a therapeutically effective amount of a compound of formula I–VII.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, and 5-hexenyl.

The term "alkoxy," as used herein, refers to an alkyl group, as defined herein, appended to the parent molecular moiety through an oxygen, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino," as used herein, refers to a —$NZ_1Z_2$ group wherein $Z_1$ and $Z_2$ are independently selected from hydrogen and alkyl.

The term "aminoalkyl," as used herein, refers to an amino group, as defined herein, appended to the parent molecular moiety through an alkyl group, as defined herein. Representative examples of aminoalkyl include, but are not limited, aminomethyl, 2-(amino)ethyl, and dimethylaminomethyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "halo" or "halogen," as used herein, refers to —Cl, —Br, —I or —F.

The term "hydroxy," as used herein, refers to an —OH group.

The term "hydroxyalkyl," as used herein, refers to one or two hydroxy groups, as defined herein, appended to the parent molecular moiety through an alkyl group, as defined herein. Representative examples of hydroxyalkyl include, but are not limited to, hydroxymethyl, 2-hydroxyethyl, 2-hydroxypropyl, 2,3-dihydroxypropyl, and 3-hydroxypropyl.

The term "nitro," as used herein, refers to a —NO$_2$ group.

Preferred compounds of formula I include, but are not limited to:

(+) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(−) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(+) 3-[4-(1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(−) 3-[4-(1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(+) 3-[4-(1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(−) 3-[4-(1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(−) 3-[2-(10-methoxy-1,2,4a,5-tetrahydropyrazino[2,1-c][1,4]benzoxazin-3(4H)-yl)ethyl]pyrido[2',3':4,5]thieno[3,2-d]pyrimidine-2,4(1H,3H)-dione;

(+) 3-[2-(10-methoxy-1,2,4a,5-tetrahydropyrazino[2,1-c][1,4]benzoxazin-3(4H)-yl]ethyl]-8-chloropyrazino[2',3':4,5]thieno[3,2-d]pyrimidine-2,4(1H,3H)-dione;

(−) 3-[3-(10-methoxy-1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]-8-chloropyrazino[2',3':4,5]thieno[3,2-d]pyrimidine-2,4(1H,3H)-dione;

(−) 3-[2-(10-methoxy-1,2,4a,5-tetrahydropyrazino[2,1-c][1,4]benzoxazin-3(4H)-yl)ethyl]-8-chloropyrazino[2',3':4,5]thieno[3,2-d]pyrimidine-2,4(1H,3H)-dione;

(+) 3-[4-(10-methoxy-1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(+) 3-[4-(10-methoxy-1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(+) 3-[2-(10-methoxy-1,2,4a,5-tetrahydropyrazino[2,1-c][1,4]benzoxazin-3(4H)-yl)ethyl]pyrido[2',3':4,5]thieno[3,2-d]pyrimidine-2,4(1H,3H)-dione;

(+) 3-[3-(10-methoxy-1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione and pharmaceutically acceptable salts thereof.

Abbreviations

Abbreviations which have been used in the descriptions of the Schemes and the Examples that follow are: Ac for acetyl; cbzCl for benzyl chloroformate; DMF for N,N-dimethylformamide; LAH for lithium aluminum hydride; and THF for tetrahydrofuran.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–2.

Scheme 1

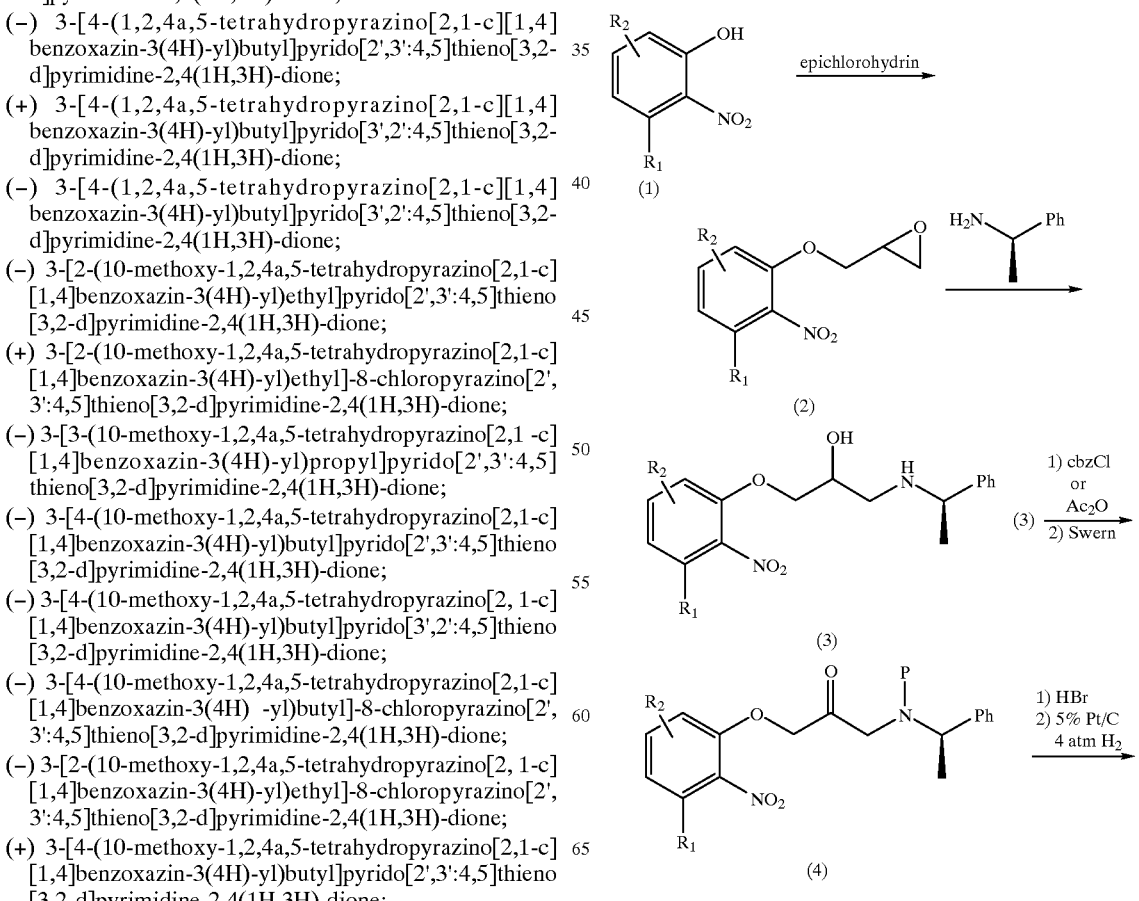

-continued

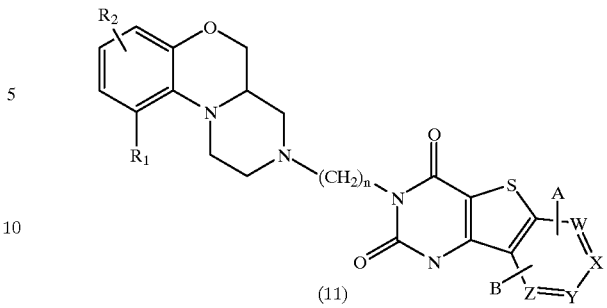

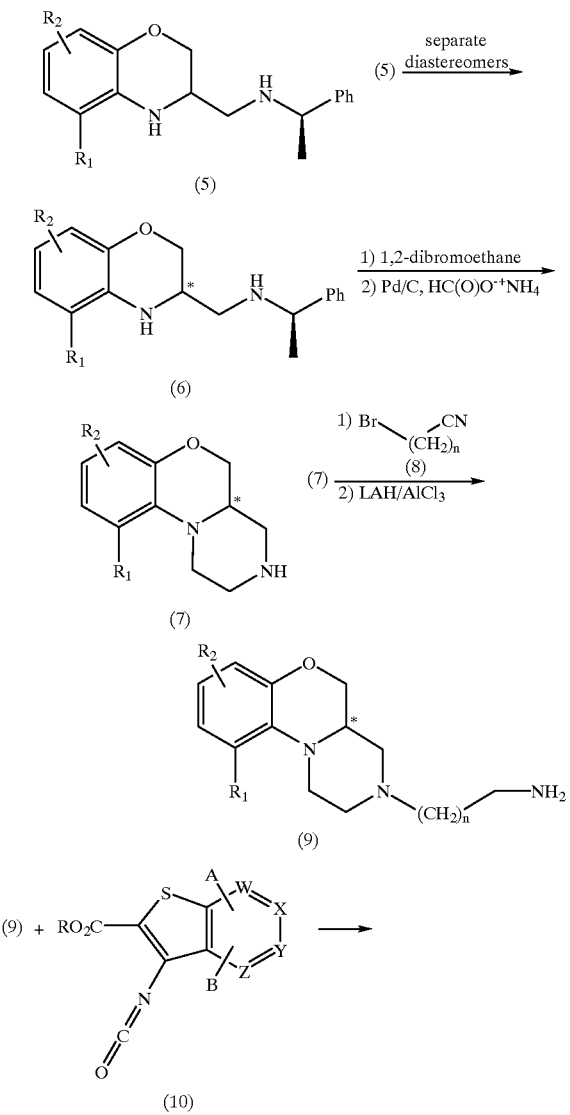

Benzoxazines of general formula (11), wherein $R_1$, $R_2$, A, B, and n are as defined in formula I and wherein W, X, Y, and Z are CH; or one of W, X, Y, or Z is N; or both W and Z are N; can be prepared as described in Scheme 1. 2-Nitrophenols of general formula (1), purchased or prepared using known methodology, can be treated with epichlorohydrin as described in (Gupta et al., Indian Journal of Chemistry 13, 462–467 (1975); and Petrov & Stephenson, Journal Of Pharmacology, 5, (1953) pp 359–369) to provide epoxides of general formula (2). Epoxides of general formula (2) can be treated with (S) or (R) α-methylbenzylamine to provide alcohols of general formula (3). Alcohols of general formula (3) can be treated with acetic anhydride or benzyl chloroformate and then oxidized under Swern conditions to provide ketones of general formula (4). Ketones of general formula (4) can be treated with 30% HBr in acetic acid and then treated with 5% platinum on carbon under 4 atmospheres of hydrogen to provide benzoxazines of general formula (5). The diastereomers, (5), can be separated via standard flash chromatography. The separated diastereomers, (6), can be treated with 1,2-dibromoethane and then treated with palladium on carbon and ammonium formate to provide enantiomerically pure hexahydropyrazino-benzoxazines of general formula (7). Hexahydropyrazinobenzoxazines of general formula (7) can be treated with bromoalkylnitriles, (8), and then treated with lithium aluminum hydride and aluminum chloride to provide amines of general formula (9). Amines of general formula (9) can be treated with isocyanates of general formula (10) from Scheme 2, wherein R is alkyl such as methyl or ethyl, to provide benzoxazines of general formula (11).

Scheme 2

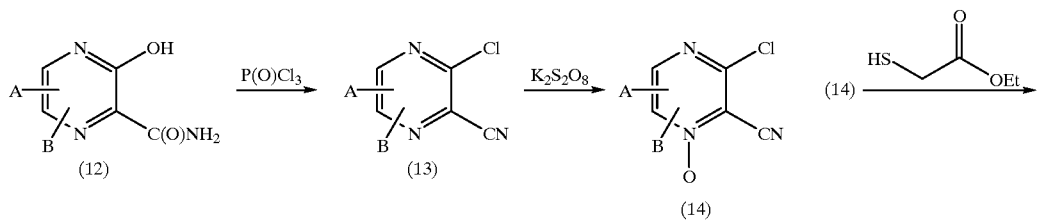

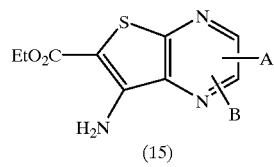

-continued

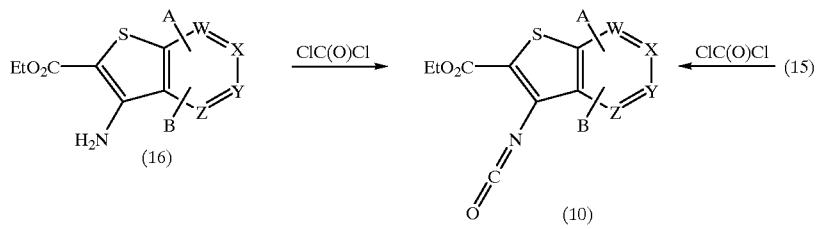

Isocyanates of general formula (10), wherein A and B are as defined in formula I and wherein W and Z are N can be prepared as described in Scheme 2. Pyrazines of general formula (12), prepared as described in (Muehlman, F. L. and Day, A. R., JACS 78 (1956) 242), can be treated with phosphorous oxychloride as described in (Chem. Abstr., 56 (1962) 871 1 h) to provide 3-chloro-2-cyanopyrazines of general formula (13). 3-Chloro-2-cyanopyrazines of general formula (13) can be oxidized with potassium persulfate to provide N-oxides of general formula (14). N-oxides of general formula (14) can be treated with ethyl thioglycolate to provide 7-aminothienopyrazines of general formula (15). 7-Aminothienopyrazines of general formula (15) can be treated with phosgene to provide isocyanates of general formula (10) wherein W and Z are both N.

Isocyanates of general formula (10), wherein A and B are as defined in formula I and wherein W, X, Y, and Z are CH; or one of W, X, Y, or Z is N; or both W and Z are N; can be prepared as described in Scheme 2. Aminothienopyridines of general formula (16) wherein W, X, Y, and Z are CH; or one of W, X, Y, or Z is N; may be prepared as described in (Beck, JOC 37 (1972) 3224; Norman, M. H. et. al., J.Med.Chem., (1996) 4692–4703; and Dunn, A. D. and Norrie, R., J.Het.Chem., 24 (1987) 85–89), and can be treated with phosgene to provide isocyanates of general formula (10).

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be had by reference to the Examples herein below. However, other equivalent separation or isolation procedures could, of course, also be used.

EXAMPLE 1

(+) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione dihydrochloride

EXAMPLE 1A

2-[(2-nitrophenoxy)methyl]oxirane

The title compound was prepared as described in (Gupta et al., Indian Journal of Chemistry 13, 462–467 (1975); and Petrov & Stephenson, Journal Of Pharmacology, 5, (1953) pp 359–369).

EXAMPLE 1B 1-(2-nitrophenoxy)-3-{[(1R)-1 -phenylethy]amino}-2-propanol

The product from Example 1A (18.3 g, 93.8 mmol) and (R) α-methylbenzylamine (14.8 g, 122 mmol) were processed according to (Gupta et al., Indian Journal of Chemistry 13, 462–467 (1975); and Petrov & Stephenson, Journal Of Pharmacology, 5, (1953) pp 359–369) to provide the title compound.

EXAMPLE 1C benzyl 2-hydroxy-3-(2-nitrophenoxy)propyl[(1R)-1-phenylethyl]carbamate The product from Example 1B (31.3 g, 100 mmol) in THF (300 mL) and 10% $Na_2CO_3$ (250 mL) at 0° C. was treated dropwise with benzyl chloroformate (18.0 g, 105 mmol), stirred vigorously for 30 minutes, and extracted with diethyl ether. The organic layer was washed with brine, dried ($MgSO_4$), and concentrated to provide the title compound.

EXAMPLE 1D benzyl 3-(2-nitrophenoxy)-2-oxopropyl[(1R)-1-phenylethyl]carbamate Oxalyl chloride (13.0 mL, 150 mmol) in dichloromethane (300 mL) at −78° C. was treated dropwise with DMSO (14.6 mL, 205 mmol), stirred for 10 minutes, treated with the product from Example 1C (46 g, 100 mmol) in dichloromethane (50 mL), stirred for 30 minutes, treated with triethylamine (55 mL, 400 mmol), warmed to 0° C. over 30 minutes, quenched with 10% $NaHCO_3$, and extracted with diethyl ether. The organic layer was washed with 10% $NaHSO_4$, 10% $NaHCO_3$ and brine, dried ($Na_2SO_4$) and concentrated. The crude product was filtered through a plug of silica gel with 7:3 hexane/ethyl acetate to provide the title compound. $^1$H NMR (300 MHz, $CDCl_3$) δ1.52 (d, 3H), 4.00 (d, 1H), 4.22 (d, 1H), 4.30 (d, 0.5H), 4.45 (d, 0.5H), 4.57 (d, 0.5H), 4.71 (d, 0.5H), 5.05–5.30 (m, 2H), 5.51 (q, 0.5H), 5.68 (q, 0.5H), 6.62 (d, 0.5H), 6.92 (d, 0.5H), 7.05 (t, 1H), 7.20–7.42 (m, 10H), 7.50 (t, 1H), 7.88 (d, 1H).

EXAMPLE 1E 1-(2-nitrophenoxy)-3-{[(1R)-1-phenylethyl]amino}acetone hydrobromide The product from Example 1D (19 g, 42.4 mmol) in 1,4-dioxane (100 mL) at 10° C. was treated with 30% HBr in acetic acid (30 mL), stirred for 30 minutes, purged with nitrogen, poured into diethyl ether (600 mL), triturated, and filtered to provide the title compound. $^1$H NMR (300 MHz, DMSO-$d_6$) δ1.60 (d, 3H), 3.98 (d, 1H), 4.20 (d, 1H), 4.38 (q, 1H), 5.14 (s, 2H), 7.16 (t, 1H), 7.25 (d, 1H), 7.40–7.55 (m, 5H), 7.63 (t, 1H), 7.91 (d,1H), 9.20–9.60 (bs, 2H).

EXAMPLE 1F (−) N-(3,4-dihydro-2H-1,4-benzoxazin-3-ylmethyl)-N-[(1R)-1-phenylethyl]amine The product from Example 1E (9.7 g, 24.5 mmol) and 5% Pt/C (2.0 g) in ethanol (1 L) was hydrogenated for 16 hours at ambient temperature under 4 atm of hydrogen, filtered through Celite® and concentrated to provide a mixture of diastereomers. The diastereomers were separated by flash chromatography on silica gel with 100:1:1 diethyl ether:ethanol:triethylamine to provide the title compound as the more mobile band. $R_f$ 0.38 (100:1:1 diethyl ether:ethanol:triethylamine); mp 91–92° C.; $[\alpha]^{23}{}_D$ −3.4° (c 1.105, CHCl$_3$); $^1$H NMR (300 MHz, CDCl$_3$) δ1.35 (d, 3H), 1.45 (bs, 1H), 2.50–2.62 (m, 2H), 3.33 (bm, 1H), 3.73 (q, 1H), 3.86 (dd, 1H), 4.15 (dd, 1H), 4.21 (bs, 1H), 6.62 (m, 2H), 6.75 (m, 2H), 7.20–7.40 (m, 5H).

EXAMPLE 1G

3-[(1R)-1-phenylethyl]-1,2,3,4,4a,5-hexahydropyrazino[2,1-c][1,4]benzoxazine

The product from Example 1F (1.5 g, 5.6 mmol), 1,2-dibromoethane (5.0 mL, 56 mmol), and diisopropylethylamine (3.0 g, 22.4 mmol) in acetonitrile (5 mL) were heated at 100° C. for 36 hours, allowed to cool to ambient temperature, and concentrated under reduced pressure. The residue was treated with 10% Na$_2$CO$_3$ and extracted with ethyl acetate. The organic layer was washed with brine, dried (Na$_2$SO$_4$) and concentrated. Flash chromatography of the residue on silica gel with 85:15 hexane:ethyl acetate provided the title compound. $^1$H NMR (300 MHz, CDCl$_3$) δ1.40 (d, 3H), 1.70 (t, 1H), 2.27 (dt, 1H), 2.68 (d, 1H), 2.83 (dt, 1H), 3.10 (t, 1H), 3.22 (d, 1H), 3.38 (q, 1H), 3.70 (d, 1H), 3.88 (dd, 1H), 4.03 (dd, 1H), 6.60–6.90 (m, 4H), 7.20–7.40 (m, 5H).

EXAMPLE 1H (+) 1,2,3 4,4a,5-hexahydropyrazino[2,1-c][1,4]benzoxazine

The product from Example 1G (1.3 g, 4.4 mmol) in methanol (75 mL) was treated with 10% Pd/C (200 mg) and ammonium formate (1.86 g, 29.5 mmol), heated at reflux for 24 hours, cooled, and filtered through Celite to provide the title compound. mp 58–59° C.; $[\alpha]^{25}{}_D$+54.4° (c 1.15, CHCl$_3$).

EXAMPLE 1I 3-(1,2,4a,5-tetrahydropyrazino[2,1-c][1,4]benzoxazin-3(4H)-yl)propanenitrile The product from Example 1H (1.5 g, 5.6 mmol), 3-bromopropanenitrile (880 mg, 6.6 mmol), and diisopropylethylamine (1.7 g, 13.0 mmol) in acetonitrile (10 mL) were heated at 100° C. for 36 hours, allowed to cool to ambient temperature, and concentrated under reduced pressure. The residue was treated with 10% Na$_2$CO$_3$ and extracted with ethyl acetate. The organic layer was washed with brine, dried (Na$_2$SO$_4$), and concentrated under reduced pressure. Flash chromatography of the residue on silica gel with 1:1 hexane:ethyl acetate provided the title compound. $^1$H NMR (300 MHz, CDCl$_3$) δ2.00 (t, 1H), 2.36 (dt, 1H), 2.55 (t, 2H), 2.73 (t, 2H), 2.85 (m, 2H), 2.97 (d, 1H), 3.22 (t, 1H), 3.69 (d, 1H), 400 (t, 1H), 4.20 (dd, 1H), 6.65–6.90 (m, 4H).

EXAMPLE 1J 3-(1,2,4a,5-tetrahydropyrazino[2,1-c [1,4]benzoxazin-3(4H)-yl)propylamine Lithium aluminum hydride (604 mg, 15.9 mmol) in diethyl ether (100 mL) was treated with aluminum chloride (707 mg, 5.3 mmol) in diethyl ether (20 mL) at 0° C., stirred for 30 minutes at ambient temperature, treated with the product from Example 1I (520 mg, 2.1 mmol) in THF (20 mL), stirred for 3 hours quenched with water (1.5 mL) treated with portions of 15% NaOH (1.5 mL) until a white solid formed and filtered through Celite® with dichloromethane. The filtrate was dried (MgSO$_4$) and concentrated under reduced pressure. The residue was chromatographed on silica gel with 89:9:1 dichloromethane:methanol:ammonium hydroxide to provide the title compound. $^1$HNMR (CDCl$_3$) δ1.63–1.73 (m, 2H), 1.70 (t, 1H), 1.95 (bs, 2H), 2.22 (dt, 1H), 2.48 (t, 2H), 2.73–2.92 (m, 4H), 3.03 (dd, 1H), 3.17 (m, 1H), 3.65 (m, 1H), 4.00 (dd, 1H), 4.20 (dd, 1H), 6.65–6.90 (m, 4H).

EXAMPLE 1K methyl 3-isocyanatothieno[3,2-b]pyridine-2-carboxylate

Methyl 3-aminothieno[3,2-b]pyridine-2-carboxylate (0.624 g, 3.00 mmol), prepared as described in (Journal of Heterocyclic Chemistry, 24: 85 (1987), and triethylamine (0.84 mL, 6.0 mmol) in THF (20 mL) at −78° C. was treated with a 1.93M solution of phosgene in toluene (1.7 mL, 3.3 mmol), stirred for 2 hours at −78° C., concentrated, and used in subsequent steps without further purification.

EXAMPLE 1L (+) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione dihydrochloride The product from Example 1J (150 mg, 0.61 mmol) and the product from Example 1K (143 mg, 0.61 mmol) in THF (20 mL) were refluxed for 6 hours, cooled, treated with 1M potassium tert-butoxide in THF (700 mL, 700 mmol), stirred for 1 hour at ambient temperature, quenched with pH 7 phosphate buffer (1 mL), and concentrated. The residue was chromatographed on silica gel with 16:1:1 ethyl acetate:formic acid:water to provide the formic acid salt which was dissolved in methanolic HCl, triturated with hot diethyl ether, and filtered to provide the desired compound. mp 278–282° C.; $[\alpha]^{26}{}_D$+11.5° (c 1.07, DMSO); $^1$H NMR (300 MHz, DMSO-d$_6$) δ2.12 (m, 2H), 2.80 (m, 1H), 3.00–3.30 (m, 4H), 3.50–3.65 (m,3H), 3.92 (dd, 1H), 4.03 (m, 3H), 4.30 (dd, 1H), 6.70–7.00 (m, 4H), 7.65 (dd, 1H)8.65 (dd, 1H), 8.85 (dd, 1H), 10.70 (bs, 1H), 12.70 (s, 1H); MS (DCI/NH$_3$) m/e 450 (M+H)$^+$; Anal. calcd for C$_{23}$H$_{23}$N$_5$O$_3$S.2.0 HCl.1.0 H$_2$O: C, 51.12; H, 5.04; N, 12.96. Found: C, 50.72; H, 4.86; N, 12.76.

EXAMPLE 2

(−) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione dihydrochloride

EXAMPLE 2A (+) N-(3 4-dihydro-2H-1,4-benzoxazin-3-ylmethyl)-N-[(1R)-1-phenylethyl]amine The title compound was isolated as the less mobile band from the diastereomeric mixture in Example 1F. $R_f$ 0.32 (100:1:1 diethyl ether:ethanol:triethylamine); $[\alpha]^{23}{}_D$+11.4°

(c 1.145, CHCl$_3$); $^1$H NMR (300 MHz, CDCl$_3$) δ1.35 (d, 3H), 1.50 (bs, 1H), 2.43 (dd, 1H), 2.67 (dd, 1H), 3.42 (bm, 1H), 3.78 (q, 1H), 3.88 (dd, 1H), 4.13 (dd, 1H), 4.21 (bs, 1H), 6.62 (m2H),6.75 (m, 2H), 7.20–7.40 (m, 5H).

EXAMPLE 2B (−) 3-[3-(1,2,4a,5-tetrahydropyrazino[2,1-c][1,4] benzoxazin-3(4H)-yl)propyl]pyrido[2',3':4,5]thieno [3,2-d]pyrimidine-2,4(1H,3H)-dione dihydrochloride The product from Example 2A was processed as described in Examples 1G-1L to provide the desired compound. mp 278–282° C.; [α]$^{23}_D$ −10.2° (c 1.33, DMSO); $^1$H NMR (300 MHz, DMSO-d$_6$) δ2.12 (m, 2H), 2.80 (m, 1H), 3.00–3.30 (m, 4H), 3.50–3.65 (m, 3H), 3.92 (dd, 1H), 4.03 (m, 3H), 4.30 (dd, 1H), 6.70–7.00 (m, 4H), 7.65 (dd, 1H), 8.65 (dd, 1H), 8.85 (dd, 1H), 10.70 (bs, 1H), 12.70 (s, 1H); MS (DCI/NH$_3$) m/e 450 (M+H)$^+$; Anal. calcd for C$_{22}$H$_{23}$N$_5$O$_3$S.2.0 HCl: C, 52.88; H, 4.82; N, 13.40. Found: C, 52.82; H, 4.68; N, 13.21.

EXAMPLE 3

(+) 3-[4-(1,2,4a,5-tetrahydropyrazino[2,1-c][1,4] benzoxazin-3(4H)-yl)butyl]pyrido[2', 3':4,5]thieno [3,2-d]pyrimidine-2,4(1H,3H)-dione dihydrochloride The product from Example 1H was processed as described in Examples 1I–1L, except substituting 4-bromobutanenitrile for 3-bromopropanenitrile, to provide the title compound. mp 278–280° C.; [α]$^{23}_D$ +10.1° (c 1.72, DMSO); $^1$H NMR (300 MHz, DMSO-d$_6$) δ1.60–1.84 (m, 4H), 2.80 (m, 1H), 3.00–3.22 (m, 4H), 3.50–3.65 (m, 3H), 3.90–4.10 (m, 4H), 4.30 (dd, 1H), 6.70–7.00 (m, 4H), 7.65 (dd, 1H), 8.65 (dd, 1H), 8.85 (dd, 1H), 10.78 (bs, 1H), 12.63 (s, 1H); MS (DCI/NH$_3$) m/e 464 (M+H)$^+$; Anal. calcd for C$_{24}$H$_{25}$N$_5$O$_3$S.2.0 HCl.0.6 H$_2$O: C, 52.67; H, 5.19; N, 12.80. Found: C, 52.43; H, 4.89; N, 12.55.

EXAMPLE 4

(−) 3-[4-(1.2,4a,5-tetrahydropyrazino[2,1-c][1, 4benzoxazin-3(4H)-yl)butyl]pyrido[2',3':4,5]thieno [3,2-d]pyrimidine-2,4(1H,3H)-dione dihydrochloride The product from Example 2A was processed as described Examples 1G–L, except substituting 4-bromobutanenitrile for 3-bromopropanenitrile, to provide the title compound. mp 282–284° C.; [α]$^{26}_D$ −11.0° (c 1.19, DMSO); $^1$H NMR (300 MHz, DMSO-d$_6$) δ1.60–184 (m, 4H), 2.80 (m, 1H), 3.00–3.22 (m, 4H), 3.50–3.65 (m, 3H), 3.90–4.10 (m, 4H), 4.30 (dd,1H), 6.70–7.00 (m, 4H), 7.65 (dd, 1H), 8.65 (dd, 1H), 8.85 (dd, 1H), 10.78 (bs, 1H), 12.63 (s, 1H);MS (DCI/NH$_3$) m/e 464 (M+H)$^+$; Anal. calcd for C$_{24}$H$_{25}$N$_5$O$_3$S.2.0 HCl: C, 53.73; H, 5.07; N, 13.05. Found: C, 53.69; H, 5.01; N, 13.22.

EXAMPLE 5

(+) 3-[4-(1,2,4a,5-tetrahydropyrazino[2,1-c][1,4] benzoxazin-3(4H)-yl)butyl]pyrido[3', 2':4,5]thieno [3,2-d]pyrimidine-2,4(1H,3H)-dione

EXAMPLE 5A methyl 3-isocyanatothieno[2,3-b]pyridine-2-carboxylate

Methyl 3-amino-thieno[2,3-b]pyridine-2-carboxylate, prepared as described in (Journal of Heterocyclic Chemistry, 24: 85 (1987)), was processed as described in Example 1K to provide the title compound.

EXAMPLE 5B (+) 3-[4-(1,2,4a,5-tetrahydropyrazino[2,1-c][1,4] benzoxazin-3(4H)-yl)butyl]pyrido[3', 2':4,5]thieno [3,2-d]pyrimidine-2,4(1H,3H)-dione dihydrochloride The product from Example 5A and the product from Example 1H were processed as described in Examples 1I–1L, except substituting 4-bromobutanenitrile for 3-bromopropanenitrile, to provide the title compound. mp 288–291° C.; [α]$^{23}_D$ +14.2° (c 1.29, DMSO); $^1$H NMR (300 MHz, DMSO-d$_6$) δ1.60–1.84 (m, 4H), 2.82 (m, 1H), 3.00–3.22 (m, 4H), 3.50–3.65 (m, 3H), 3.90–4.10 (m, 4H), 4.30 (dd, 1H), 6.70–7.00 (m, 4H), 7.65 (dd,1H), 8.76 (dd, 1H), 8.81 (dd, 1H), 10.50 (bs, 1H), 12.70 (s, 1H); MS (DCI/NH$_3$) m/e 464 (M+H)$^+$; Anal. calcd for C$_{24}$H$_{25}$N$_5$O$_3$S.HCl.0.2 H$_2$O: C, 57.24; H, 5.28; N, 13.91. Found: C, 57.06; H, 5.21; N, 13.67.

EXAMPLE 6

(−) 3-[4-(1,2,4a,5-tetrahydropyrazino[2,1-c][1,4] benzoxazin-3(4H)-yl)butyl]pyrido[3', 2':4,5]thieno [3,2-d]pyrimidine-2,4(1H,3H)-dione dihydrochloride The product from Example 2A and the product from Example 5A were processed as described in Examples 1I–1L, except substituting 4-bromobutanenitrile for 3-bromopropanenitrile, to provide the title compound. mp 290–293° C.; [α]$^{23}_D$ −13.6° (c 1.41, DMSO); $^1$H NMR (300 MHz, DMSO-d$_6$) δ1.60–1.84 (m, 4H), 2.82 (m, 1H), 3.00–3.22 (m, 4H), 3.50–3.65 (m, 3H),3.90–4.10 (m, 4H), 4.30 (dd, 1H), 6.70–7.00 (m, 4H), 7.65 (dd, 1H), 8.76 (dd, 1H), 8.81 (dd, 1H), 10.95 (bs, 1H), 12.70 (s, 1H); MS (DCI/NH$_3$) m/e 464 (M+H)$^+$; Anal. calcd for C$_{24}$H$_{25}$N$_5$O$_3$S.2.0 HCl: C, 57.65; H, 5.24; N, 14.01. Found: C, 57.33; H, 5.20; N, 13.73.

EXAMPLE 7

(−) 3-[2-(10methoxy-1,2,4a,5-tetrahydropyrazino[2, 1-c][1,4]benzoxazin-3(4H)-yl)ethyl]pyrido[2',3':4,5] thieno[3,2-d]pyrimidine-2,4(1H,3H)-dione dihydrochloride

EXAMPLE 7A

2-[(3-methoxy-2-nitrophenoxy)methyl]oxirane

2-Nitro-3-methoxyphenol, prepared as described in (U.S. Pat. No. 2,385,282) was processed as described in (Gupta et al., Indian Journal of Chemistry 13, 462–467 (1975); and Petrov & Stephenson, Journal Of Pharmacology, 5, (1953) pp 359–369) to provide the title compound. $^1$H NMR (300 MHz, CDCl$_3$) δ2.72 (dd, 1H), 2.88 (t, 1H), 3.32 (m, 1H), 3.88 (s, 3H), 4.10 (dd, 1H), 4.30 (dd, 1H), 6.54 (d, 1H), 6.56 (d, 1H), 7.33 (t, 1H).

EXAMPLE 7B 1-(3-methoxy-2-nitrophenoxy)-3-{[(1R)-1-phenylethyl]amino }-2-propanol hydrobromide The product from Example 7A was processed as described in Examples 1B-1E to provide the title compound.

¹H NMR (300 MHz, DMSO-d₆) δ1.60 (d, 3H), 3.86 (s, 3H), 3.90 (bd, 1H), 4.12 (bd, 1H), 4.36 (q, 1H), 5.10 (s, 2H), 6.75 (d, 1H), 6.93 (d, 1H), 7.40–7.55 (m, 6H), 9.20–9.60 (bs, 2H).

EXAMPLE 7C

N-[3-(3-methoxy-2-nitrophenoxy)-2-oxopropyl]-N-[(1R)-1-phenylethyl]acetamide

The product from Example 7B (33.0 g, 77.6 mmol) in dichloromethane (600 mL) at 0 ° C. was treated sequentially with acetyl chloride (6.4 g, 81.0 mmol) and triethylamine (23.6 g,233 mmol) in dichloromethane (50 mL), stirred for 1 hour at 0° C., and quenched with 1M NaOH. The organic layer was washed with brine, dried (MgSO₄), and concentrated to provide the title compound. ¹H NMR (300 MHz, CDCl₃) δ1.60 (d, 3H), 2.29 (s, 3H), 3.70 (d, 1H),3.86 (s, 3H), 4.14 (d, 1H), 4.55 (d, 1H), 4.73 (d, 1H), 5.15 (q, 1H), 6.55 (d, 1H), 6.65 (d, 1H), 7.20–7.42 (m, 6H).

EXAMPLE 7D

N-[(5-methoxy-3,4-dihydro-2H-1,4-benzoxazin-3-yl)methyl]-N-[(1R)-1-phenylethyl]acetamide The product from Example 7C was processed as described in Example 1F to provide the title compound. ¹H NMR (300 MHz, DMSO-d₆) δ1.60 (d, 3H), 3.86 (s, 3H), 3.90 (bd, 1H), 4.12 (bd, 1H), 4.36 (q, 1H), 5.10 (s, 2H), 6.75 (d, 1H), 6.93 (d, 1H), 7.40–7.55 (m, 6H), 9.20–9.60 (bs, 2H).

EXAMPLE 7E

N-[(5-methoxy-3,4-dihydro-2H-1,4-benzoxazin-3-yl)methyl]-N-[(1R)-1-phenylethyl]amine The product from Example 7D (24.8 g, 72.9 mmol) in 2.0M HCl (500 mL) was refluxed for 16 hours, cooled, concentrated to a volume of 100 mL, basified to pH 14 with 50% NaOH and extracted with ethyl acetate. The organic layer was dried (MgSO₄) and concentrated. The residue was chromatographed on silica gel with ethyl acetate to provide two diastereomers, $R_f$ 0.62 (ethyl acetate) and $R_f$ 0.60 (ethyl acetate). ¹H NMR (300 MHz, CDCl₃, for $R_f$ 0.62) δ1.35 (d, 3H), 1.55 (bs, 1H), 2.50–2.62 (m, 2H), 3.33 (bm, 1H), 3.73 (q, 1H), 3.83 (s, 3H), 3.90 (dd, 1H), 4.18 (dd, 1H), 4.35 (bs, 1H), 6.43 (m, 2H), 6.59 (t, 1H), 7.20–7.40 (m, 5H).

¹H NMR (300 MHz, CDCl₃, for $R_f$ 0.60) δ1.40 (d, 3H), 1.55 (bs, 1H), 2.52 (dd, 1H), 2.73 (dd, 1H), 3.48 (bm, 1H), 3.83 (q, 1H), 3.84 (s, 3H), 3.95 (dd, 1H), 4.16 (dd, 1H), 4.38 (bs, 1H), 6.43 (m, 2H), 6.59 (t, 1H), 7.20–7.40 (m, 5H).

EXAMPLE 7F (−) 3-[2-(10-methoxy-1,2,4a,5-tetrahydropyrazino[2,1.-c][1,4]benzoxazin-3 (4H) -yl)ethyl]pyrido[2', 3':4,5']thieno[3,2-d]pyrimidine-2,4(1H,3H)-dione dihydrochloride The more mobile product ($R_f$ 0.62) from Example 7E was processed according to Examples 1G–1L, except substituting bromoacetonitrile for 3-bromopropanenitrile, to provide the title compound. mp 297–298° C.; $[\alpha]^{23}_D$ −21.1° (c 1.12, DMSO); ¹H NMR (300 MHz, DMSO-d₆) δ3.00–3.75 (m, 8H), 3.79 (s, 3H), 3.85–4.77 (m, 5H), 6.48 (dd, 1H), 6.58 (dd, 1H), 6.83 (t, 1H), 7.65 (dd, 1H), 8.65 (dd, 1H), 8.85 (dd, 1H), 10.60 (bs, 1H), 12.80 (s, 1H); MS(DCI/NH₃) m/e 466 (M+H)⁺; Anal. calcd for C₂₃H₂₃N₅O₄S.2.0 HCl.0.6 H₂O: C, 49.27; H, 4.60; N, 12.50. Found: C, 49.36; H, 4.73; N, 12.16.

EXAMPLE 8

(+) 3-[2-(10-methoxy-1,2,4a,5-tetrahydropyrazino[2,1-c][1,4]benzoxazin-3(4H)-yl)ethyl]-8-chloropyrazino[2',3':4,5]thieno[3,2-d]pyrimidine-2,4(1H,3H)-dione dihydrochloride

EXAMPLE 8A 3-chloro-2-cyanopyrazine-1-oxide

2-Chloro-3-cyanopyrazine (5.00 g, 35.94 mmol) in concentrated H₂SO₄ (35 mL) at 0° C. was treated portionwise with K₂S₂O₈ (11.65 g, 43.95 mmol), warmed to room temperature, stirred for 24 hours, treated with water, and extracted with chloroform. The organic extract was washed sequentially with water, saturated NaHCO₃ and brine, dried (MgSO₄) and concentrated to provide the title compound. MS (DCI/NH₃) m/e 173 (M+NH₄)⁺.

EXAMPLE 8B ethyl 7-amino-1-oxido-thieno[2,3-b]pyrazine-6-carboxylate

The product from Example 8A (2.90 g, 18.64 mmol) in DMF (100 mL) was treated with ethyl thioglycolate (2.24 g, 18.64 mmol), cooled to 0° C., treated with solid sodium ethoxide (2.54 g, 37.29 mmol), warmed to room temperature, stirred for 13 hours, treated with brine, and extracted with ethyl acetate. The organic extract was washed with water and brine, dried (MgSO₄), and concentrated. The residue was purified by flash chromatography on silica gel with 2:1 then 1:1 hexanes/ethyl acetate to provide the title compound. MS (DCI/NH₃) m/e 240 (M+H)⁺ vand 257 (M+NH₄)⁺.

EXAMPLE 8C ethyl 7-amino-2-chlorothieno[2,3-b]pyrazine-6-carboxylate

The product from Example 8B (0.88 g, 3.68 mmol) in POCl₃ (50 mL) was heated to 95° C. for 3 hours, concentrated, treated with water, and extracted with ethyl acetate. The extract was washed sequentially with water, saturated NaHCO₃ and brine, dried (Na₂SO₄), and concentrated. The residue was purified by flash chromatography on silica gel with 10:1 to 1:1 hexanes/ethyl acetate to provide the title compound. MS (DCI/NH₃) m/e 258 (M+H)⁺ and 275 (M+NH₄)⁺.

EXAMPLE 8D ethyl 2-chloro-7-isocyanatothieno[2,3-b]pyrazine-6-carboxylate

The product from Example 8C was processed as described in Example 1K to provide the title compound.

EXAMPLE 8E 2-(10-methoxy-1,2,4a,5-tetrahydropyrazino[2,1-c][1,4]benzoxazin-3(4H)-yl)ethylamine The less mobile product from Example 7E was processed as described Examples 1G–1J, except substituting bromoacetonitrile for 3-bromopropanenitrile, to provide the title compound.

EXAMPLE 8F (+) 3-[2-(10-methoxy-1,2,4a,5-tetrahydropyrazino[2.1-c][1,4]benzoxazin-3(4H)-yl)ethyl]-8-chloropyrazino[2',3':4,5]thieno[3,2-d]pyrimidine-2,4(1H, 3H)-dione dihydrochloride The product from Example 8D and the product from Example 8E were processed as described in Example 1L to provide the title compound. mp 280–283° C.; $[\alpha]^{23}_D$ +19.30° (c 1.03, DMSO); ¹H NMR (300 MHz, DMSO-d₆) δ2.95–3.80 (m, 7H), 3.80 (s, 3H), 3.86–4.75(m, 6H), 6.44–6.95 (m, 3H), 9.03 (s, 1H), 10.80 (bs, 1H), 13.03 (s, 1H); MS (DCI/NH$_3$) m/e 501 (M+H)$^+$; Anal. calcd for C$_{22}$H$_{21}$N$_6$O$_4$SCl.2.2 HCl: C, 45.47; H, 4.02; N, 14.46. Found: C, 45.44; H, 3.81; N, 14.34.

EXAMPLE 9

(−) 3-[3-(10-methoxy-1,2,4a,5-tetrahydropyrazino[2, 1-c][1,4]benzoxazin-3(4H)-yl)propyl]pyrido[2',3':4, 5]thieno[3,2-d]pyrimidine-2,4(1H, 3H)-dione trihydrochloride The more mobile product from Example 7E was processed as described in Examples 1–G–1L to provide the desired compound. mp 215–220° C.; [α]$^{25}_D$ −7.6° (c 1.10, DMSO); $^1$HNMR (300 MHz, DMSO-d$_6$) δ2.15 (m, 2H), 2.90 (m, 1H), 2.98–3.30 (m, 4H), 3.33–3.75 (m,3H), 3.78 (s, 3H), 3.88 (dd, 1H), 4.02 (m, 2H), 4.17 (dd, 1H), 4.60 (m,1H), 6.48 (dd, 1H), 6.58 (dd, 1H), 6.83 (t, 1H), 7.65 (dd, 1H), 8.65 (dd, 1H), 8.85 (dd, 1H), 10.90 (bs,1 H), 12.65(s, 1H); MS (DCI/NH3) m/e 480 (M+H)$^+$; Anal. calcd for C$_{24}$H$_{25}$N$_5$O$_4$S.3.0 HCl: C, 48.95; H, 4.79; N, 11.89. Found: C, 49.22; H, 4.65; N, 11.87.

EXAMPLE 10

(−) 3-[3-(10-methoxy-1,2,4a,5-tetrahydropyrazino[2, 1-c][1,4]benzoxazin-3(4H)-yl)butyl]pyrido[2',3':4,5] thieno[3,2-d]pyrimidine-2,4(1H,3H)-dione trihydrochloride The more mobile product from Example 7E was processed as described in Examples 1G–1L, except substituting 4-bromobutanenitrile for 3-bromopropanenitrile, to provide the title compound. mp 274–278° C.; [α]$^{23}_D$ −8.4° (c 1.13, DMSO); $^1$H NMR (300 MHz, DMSO-d$_6$) δ1.60–1.84 (m, 4H), 2.90 (m, 1H), 3.00–3.22 (m, 4H), 3.40–3.65 (m, 3H), 3.75 (s, 3H), 3.85–4.22 (m, 4H), 4.60 (m, 1H), 6.48 (dd, 1H), 6.58 (dd, 1H), 6.83 (t, 1H), 7.65 (dd, 1H), 8.65 (dd, 1H), 8.85 (dd, 1H), 10.90 (bs, 1H), 12.65 (s, 1H); MS (DCI/NH$_3$) m/e 494 (M+H)$^+$; Anal. calcd for C$_{25}$H$_{27}$N$_5$O$_4$S.3 HCl.0.5 H$_2$O: C, 49.07; H, 5.11; N, 11.44. Found: C, 49,25; H, 5.00; N, 11.41.

EXAMPLE 11

(−) 3-[3-(10-methoxy-1,2,4a,5-tetrahydropyrazino[2, 1-c][1,4]benzoxazin-3(4H)-yl)butyl]pyrido[3',2':4,5] thieno[3,2-d]pyrimidine-2,4(1H,3H)-dione trihydrochloride

EXAMPLE 11A 4-(10-methoxy-1,2,4a,5-tetrahydropyrazino[2,1-c][1, 4]benzoxazin-3(4H)-yl)butylamine The more mobile product from Example 7E was processed as described in Examples 1G–1J, except substituting 4-bromobutanenitrile for 3-bromopropanenitrile to provide the title compound.

EXAMPLE 11B (−) 3-[4-(10-methoxy-1,2,4a,5-tetrahydropyrazino[2, 1-c][1,4]benzoxazin-3(4H)-yl)butyl]pyrido[3',2':4.5] thieno[3,2-d]pyrimidine-2,4(1H,3H)-dione trihydrochloride The product from Example 11A and the product from Example 5A were processed as described in Example 1L to provide the title compound. mp 207–210° C; [α]$^{23}_D$ −8.8° (c 1.03, DMSO); $^1$H NMR (300 MHz, DMSO-d$_6$) δ1.60–1.84 (m, 4H), 2.90 (m, 1H), 3.00–3.22 (m, 4H), 3.40–3.65 (m, 3H), 3.75 (s, 3H), 3.85–4.22 (m, 4H), 4.60 (m, 1H), 6.48 (dd, 1H), 6.58 (dd, 1H), 6.83 (t, 1H), 7.65 (dd, 1H), 8.76–8.82 (m, 2H), 10.70 (bs, 1H), 12.75 (s, 1H); MS (DCI/NH$_3$) m/e 494 (M+H)$^+$; Anal. calcd for C$_{25}$H$_{27}$N$_5$O$_4$S.2.0 HCl.0.5 H$_2$O: C, 52.18; H, 5.25; N, 12.17. Found: C, 52.01; H, 5.29; N, 11.97.

EXAMPLE 12

(−) 3-[4-(10-methoxy-1,2,4a,5-tetrahydropyrazino[2, 1-c][1,4]benzoxazin-3(4H)-yl)butyl]-8-chloropyrazino[2',3':4,5]thieno[3,2-d]pyrimidine-2,4 (1H,3H)-dione dihydrochloride The product from Example 11A and the product from Example 8D were processed as described in Example 1L to provide the title compound. mp 198–201° C.; [α]$^{23}_D$ −7.8 °(c 1.02, DMSO); $^1$H NMR (300 MHz, DMSO-d$_6$) δ1.60–1.85 (m, 4H), 2.80–3.75 (m, 7H), 3.78 (s,3H), 3.82–4.75 (m, 6H), 6.42–6.95 (m, 3H), 9.02 (s, 1H), 10.60 (bs, 1H), 1290 (s, 1H); MS (DCI/NH$_3$) m/e 529 (M+H)$^+$; Anal. calcd for C$_{24}$H$_{25}$N$_6$O$_4$SCl.2.0 HCl: C, 47.89; H, 4.52; N, 13.96. Found: C, 47.64; H, 4.62; N, 13.63.

EXAMPLE 13

(−) 3-[4-(10-methoxy-1,2,4a,5-tetrahydropyrazino[2, 1-c][1,4]benzoxazin-3(4H)-yl)ethyl]-8-chloropyrazino[2',3':4,5]thieno[3,2-d]pyrimidine-2,4 (1H,3H)-dione dihydrochloride

EXAMPLE 13A 2-(10-methoxy-1,2,4a,5-tetrahydropyrazino[2,1-c][1, 4]benzoxazin-3(4H)-yl)ethylamine The more mobile product from Example 7E was processed as described Examples 1G–1J, except substituting bromoacetonitrile for 3-bromopropanenitrile, to provide the title compound.

EXAMPLE 13B (−) 3-[2-(10-methoxy-1,2,4a,5-tetrahydropyrazino[2, 1-c][1,4]benzoxazin-3(4H)-yl)ethyl]-8-chloropyrazino[2',3':4,5]thieno[3,2-d]pyrimidine-2,4 (1H,3H)-dione dihydrochloride The product from Example 13A and the product from Example 8D were processed as described in Example 1L to provide the title compound. mp 280–282° C.; [α]$^{23}_D$ −20.9° (c 1.15,DMSO); $^1$H NMR (300 MHz, DMSO-d$_6$) δ2.95–3.80 (m, 7H), 3.80 (s, 3H), 3.86–4.75 (m,6H), 6.44–6.95 (m, 3H), 9.03 (s, 1H), 10.80 (bs, 1H), 13.03 (s, 1H); MS (DCI/NH$_3$) m/e 501 (M+H)$^+$; Anal. calcd for C$_{22}$H$_{21}$N$_6$O$_4$SCl.2.4 HCl: C, 44.90; H, 4.01; N, 14.28. Found: C, 44.91; H, 3.70; N, 14.16.

EXAMPLE 14

(+) 3-[4-(10-methoxy-1,2,4a,5-tetrahydropyrazino[2, 1-c][1,4]benzoxazin-3(4H)-yl)butyl]pyido [2',3':4,5] thieno[3,2-d]pyrimidine-2,4(1H,3H)-dione trihydrochloride The less mobile product from Example 7E was processed as described Examples 1G–1L, except substituting 4-bromobutanenitrile for 3-bromopropanenitrile, to provide the title compound. mp 280–282° C.; $[\alpha]^{23}{}_D$+9.0° (c 1.00, DMSO); $^1$H NMR (300 MHz, DMSO-d$_6$) δ1.60–1.84 (m, 4H), 2.90 (m, 1H), 3.00–3.22 (m, 4H), 3.40–3.65 (m, 3H), 3.75 (s, 3H), 3.85–4.22 (m, 4H), 4.60 (m, 1H), 6.48 (dd, 1H), 6.58 (dd, 1H), 6.83 (t, 1H), 7.65 (dd, 1H), 8.65 (dd, 1H), 8.85 (dd,1H), 10.30 (bs, 1H), 12.65 (s, 1H); MS (DCI/NH$_3$) m/e 494 (M+H)$^+$; Anal. calcd for C$_{25}$H$_{27}$N$_5$O$_4$S.3 HCl: C, 49.80; H, 5.02; N, 11.61. Found: C, 49.87; H, 4.83; N, 11.38.

EXAMPLE 15

(+) 3-[4-(10-methoxy-1,2,4a,5-tetrahydropyrazino[2, 1-c][1,4]benzoxazin-3(4H)-yl)butyl]pyrido[3',2':4,5] thieno[3,2-d]pyrimidine-2,4(1H,3H)-dione trihydrochloride

EXAMPLE 15A 4-(10-methoxy-1,2,4a,5-tetrahydropyrazino [2,1-c] [1,4]benzoxazin-3 (4H)-yl)butylamine The less mobile product from Example 7E was processed as described in Examples 1G–1J, except substituting 4-bromobutanenitrile for 3-bromopropanenitrile to provide the title compound.

EXAMPLE 15B (+) 3-[4-(10-methoxy-1,2,4a,5-tetrahydropyrazino[2, 1-c][1,4]benzoxazin-3(4H)-yl)butyl]pyrido[3',2':4,5] thieno[3,2-d]pyrimidine-2,4(1H,3H)-dione trihydrochloride The product from Example 15A and the product from Example 5A was processed as described in Example 1L to provide the title compound. mp 225–230° C.; $[\alpha]^{23}{}_D$+9.1° (c 1.03, DMSO); $^1$H NMR (300 MHz, DMSO-d$_6$) δ1.60–1.84 (m, 4H), 2.90 (m, 1H), 3.00–3.22 (m,4H), 3.40–3.65 (m, 3H), 3.75 (s, 3H), 3.85–4.22 (m, 4H), 4.60 (m, 1H), 6.48 (dd, 1H), 6.58 (dd, 1H), 6.83 (t, 1H), 7.65 (dd, 1H), 8.76–8.82 (m, 2H), 10.90 (bs, 1H), 12.75 (s, 1H); MS (DCI/NH$_3$) m/e 494 (M+H)$^+$; Anal. calcd for C$_{25}$H$_{27}$N$_5$O$_4$S.2.75 HCl: C, 50.57; H, 5.05; N,11.79. Found: C, 50.27; H, 4.93; N, 11.64.

EXAMPLE 16

(+) 3-[2-(10-methoxy-1,2,4a,5-tetrahydropyrazino[2, 1-c][1,4]benzoxazin-3(4H)-yl)ethyl]pyrido[2',3':4,5] thieno[3,2-d]pyrimidine-2,4(1H,3H)-dione trihydrochloride

EXAMPLE 16A 2-(10-methoxy-1,2,4a,5-tetrahydropyrazino[2,1-c][1, 4]benzoxazin-3(4H)-yl)ethylamine The less mobile product from Example 7E was processed as described Examples 1G–1J, except substituting bromoacetonitrile for 3-bromopropanenitrile, to provide the title compound.

EXAMPLE 16B (+) 3-[2-(10-methoxy-1,2,4a,5-tetrahydropyrazino[2, 1-c][1,4]benzoxazin-3(4H)-yl)ethyl]pyrido[2',3':4,5] thieno[3,2-d]pyrimidine-2,4(1H,3H)-dione trihydrochloride The product from Example 16A and the product from Example 1K were processed as described in Example 1L to provide the title compound. mp 301–302° C; $[\alpha]^{23}{}_D$ +21.3° (c1.12, DMSO); $^1$H NMR (300 MHz, DMSO-d$_6$) δ3.00–3.75 (m, 8H), 3.79 (s, 3H), 3.85–4.77 (m, 5H), 6.48 (dd, 1H), 6.58 (dd, 1H), 6.83 (t, 1H), 7.65 (dd, 1H), 8.65 (dd, 1H), 8.85 (dd, 1H), 10.50 (bs, 1H), 12.80 (s, 1H); MS (DCI/NH$_3$) m/e 466 (M+H)$^+$; Anal. calcd for C$_{23}$H$_{23}$N$_5$O$_4$S.3.0 HCl: C, 48.05; H, 4.56; N, 12.08. Found: C, 47.78; H, 4.80; N, 11.73

EXAMPLE 17

(+) 3-[3-(10-methoxy-1,2,4a,5-tetrahydropyrazino[2, 1-c][1,4]benzoxazin-3(4H)-yl)propyl]pyrido[2',3':4, 5]thieno[3,2-d]pyrimidine-2,4(1H,3H)-dione trihydrochloride The less mobile product from Example 7E was processed according to Examples 1G–1L to provide the desired compound, mp 219–224° C.; $[\alpha]^{25}{}_D$+8.2° (c 1.30, DMSO); $^1$H NMR (300 MHz, DMSO-d$_6$) δ2.15 (m, 2H), 2.90 (m, 1H), 2.98–3.30 (m, 4H), 3.33–3.75 (m, 3H), 3.78 (s, 3H), 3.88 (dd, 1H), 4.02 (m, 2H), 4.17 (dd, 1H), 4.60 (m,1H), 6.48 (dd, 1H), 6.58 (dd, 1H), 6.83 (t, 1H), 7.65 (dd, 1H), 8.65 (dd, 1H), 8.85 (dd, 1H), 10.44 (bs, 1H), 12.70 (s,1H); MS (DCI/NH$_3$) m/e 480 (M+H)$^+$; Anal. calcd for C$_{24}$H$_{25}$N$_5$O$_4$S.3.0 HCl: C, 48.95; H, 4.79; N, 11.89. Found: C, 48.81; H, 5.12; N, 11.62.

The foregoing is merely illustrative and is not intended to limit the invention to the disclosed compounds. Variations and changes which are obvious to one skilled in the art are to be within the scope and nature of the invention which are defined in the appended claims.

Determination of Biological Activity

Representative compounds of the present invention were evaluated for their ability to displace prazosin from its adrenoreceptor.

In vitro Binding Assays

For purposes of discussing $\alpha_1$ adrenoreceptor subtypes, the IUPHAR convention of using lower case letters to define molecular clones and upper case letters to indicate pharmacologically defined adrenoreceptors has been followed. Moreover, the newly recommended nomenclature for $\alpha_1$ receptor subtypes ($\alpha_{1a}$, $\alpha_{1b}$, $\alpha_{1d}$) has been used.

Representative compounds of the invention were evaluated for $\alpha$ adrenoreceptor binding affinity in vitro using [$^3$H]-prazosin as the radioligand and following four cloned $\alpha_1$ adrenoreceptors expressed in LTK cells: $\alpha_{1a}$ (rat), $\alpha_{1a}$ (bovine), $\alpha_{1b}$ : (hampster), and $\alpha_{1d}$ (rat).

The cDNA clones encoding the $\alpha_1$ adrenoreceptors were obtained from TULCO (Triangle Universities Licensing Consortium, Research Triangle Park, N.C.) and inserted into the eukaryotic expression vector SnaB30. In this vector, expression of the adrenoreceptor gene is under the transcriptional control of an SV40 early promoter. Positive drug selection is provided by a neomycin-resistance gene. Mouse fibroblast cells (LTK) were transfected with the $\alpha_1$ expression plasmids and grown in Dulbecco's modified Eagle's medium (DMEM) containing 10% fetal calf serum and 30 µM G418. Stable G418-resistant parental lines were generated with successful expression of adrenoreceptor protein monitored using radioligand binding techniques. Stable single cell clones derived from the parental lines were screened in adrenoreceptor binding assays to identify clones having high adrenoreceptor density. Roller bottle cultures of the cloned lines were used to provide cell membranes for subsequent adrenoreceptor binding characterization studies. A cell line containing the SnaB30 vector expressing the human erythropoietin gene served as a negative control.

For adrenoreceptor binding assays, large scale membrane preparations were utilized in which 6 million cells were seeded into small (450 cm$^2$) Coming tissue culture roller bottles. DMEM (200 mL) containing 10% fetal calf serum and 300 µM G418 were added to each roller bottle. A 95% air/5% $CO_2$ gas mixture (sterile) was injected into each roller bottle prior to sealing, and the bottles were then incubated at 37° C. on a roller rack for 5 days. Cells were refed with fresh medium after 3 days in culture.

On the fifth day of culture, growth medium was removed from cells grown in roller bottles, and the cells were washed twice with PBS (Sigma, 120 mM NaCl, 2.7 mM KCl, 10 mM $Na_2HPO_4$-$NaH_2PO_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000×G for 5 minutes at 2–4° C., washed with PBS and recentrifuged. The supernatant was decanted, and the pellet was weighed to determine the wet weight of cells. Cells were washed a final time in 40 vol 5 mM Tris-HCl, 5 mM EDTA, pH=7.7 and centrifuged at 40,000×G for 10 minutes ("vol" indicates volume/weight, e.g., a "vol" of 40 would indicate that the one gram of cells were washed with 40 mls of buffer). Cells were homogenized in of 50 mM Tris-HCl, 5 mM EDTA (pH=7.4) (10 mL) and diluted to 40 mL/tube. Homogenates were centrifuged at 40,000×G for 10 minutes. The supernatant was decanted and the pellets rehomogenized in 50 mM Tris-HCl (pH=7.4) and centrifuged as before. The supernatant was decanted and the homogenate was resuspended in 6.25 volumes (per gram wet weight) of 50 mM Tris-HCl and aliquots of the pooled homogenates frozen in liquid $N_2$ and stored at −70° C. until the time of assay.

Receptor binding assays for $\alpha_1$ adrenoreceptors were performed essentially as described by Greengrass and Bremner (Eur. J. Pharmacol. 55: 323–326 (1979)). Briefly, plastic Bioblocks® (DBM Scientific, Valencia, Calif.) were incubated at 25° C. for 50 minutes with 500 µL of membrane homogenate (diluted with an additional 96 volumes (for cloned adrenoreceptors, 12 volumes for submaxillary gland) in 50 mM Tris-HCl buffer (pH=7.7 at the time of assay), 450 µL of [$^3$H]prazosin (0.2 nM final concentration, 75–85 Ci/mmole, DuPont-NEN Corp., Boston, Mass.) and 50 µL of either water (for total binding) or 10 µM phentolamine (final concentration, for non-specific binding)). Following equilibration, bound radioligand was separated from free on GF/B filters (presoaked in 0.5% polyethyleneimine) using ither a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., J. Receptor Res. 8: 23–46 (1988)). The in Table 1.

TABLE 1

In Vitro Data for Binding to $\alpha_1$ Adrenoceptors

| Example | Radioligand Binding (Ki, nM) | | | |
|---|---|---|---|---|
| | $\alpha_{1a}$ (Rat) | $\alpha_{1a}$ (Bovine) | $\alpha_{1b}$ (Hamster) | $\alpha_{1d}$ (rat) |
| 1 | 1.84 | 1.175 | 14.304 | 5.891 |
| 2 | 19.29 | 13.77 | 24.563 | 69.757 |
| 3 | 2.851 | 2.087 | 32.382 | 4.998 |
| 4 | 6.622 | 3.604 | 26.486 | 19.509 |
| 5 | 5.017 | 2.724 | 40.619 | 4.262 |
| 6 | 9.832 | 5.508 | 27.349 | 16.905 |
| 7 | 0.864 | 0.251 | 6.889 | 1.131 |
| 8 | 1.776 | 0.463 | 58.092 | 5.076 |
| 9 | 0.359 | 0.249 | 3.862 | 1.285 |
| 10 | 0.257 | 0.243 | 1.814 | 0.344 |
| 11 | 0.24 | 0.387 | 2.715 | 0.427 |
| 12 | 0.648 | 0.41 | 8.912 | 1.153 |
| 13 | 1.546 | 0.685 | 39.103 | 3.523 |
| 14 | 0.29 | 0.243 | 8.316 | 2.16 |
| 15 | 0.447 | 0.289 | 13.77 | 1.301 |
| 16 | 1.237 | 0.334 | 11.816 | 2.014 |
| 17 | 4.443 | 2.502 | 40.377 | 20.484 |
| Prazosin | 9.95 | | 10.3 | |

These results show that the compounds of the invention bind to a, adrenoreceptors and show specificity for the $\alpha_{1a}$ adrenoreceptor relative to $\alpha_{1b}$ and $\alpha_{1d}$ receptors and therefore may have utility for the treatment of diseases requiring inhibition at the $\alpha_1$ adrenoreceptor.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in *IUPAC 1974 Recommendations for Section E, Fundamental Stereochemistry, Pure Appl. Chem.*, (1976), 45: 13–30, hereby incorporated by reference. In particular, the stereochemistry at the 4a-position of compounds of formula I may independently be either (R) or (S), unless specifically noted otherwise. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. Further included within the scope of the present invention are pharmaceutical compositions comprising one or more of the compounds of formula I–VII prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be. controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The compounds of the present invention, including but not limited to those specified in the examples, inhibit $\alpha_1$ adrenoreceptors (especially humans). As $\alpha_1$ adrenoreceptor inhibitors, the compounds of the present invention may be useful for the treatment and prevention of diseases such as benign prostatic hyperplasia, bladder outlet obstruction, neurogenic bladder, and uterine smooth muscle contraction.

The ability of the compounds of the present invention to treat benign prostatic hyperplasia, bladder outlet obstruction, neurogenic bladder, and uterine smooth muscle contraction can be demonstrated according to the methods described (Lepor, H., Alpha Blockade for the Treatment of Benign Prostatic Hyperplasia, Urol. Clin. N. Amer., 22: 375–386, 1995); (Rosier, P. F.W. M., J. J. M. C. H. de la Rosette, H. Wijkstra, Ph.E. V. Van Kerrebroeck and F. M. J. Debruyne, Is Detrusor Instability in Elderly Males Related to the Grade of Obstruction?, Neurourol. Urodynam., 14: 625–633, 1995); (Andersson, K-E., Prostatic and Extraprostatic $\alpha$ adrenoceptors Contributions to the Lower Urinary Tract Symptoms in Benign Prostatic Hyperplasia, Scand. J. Urol. and Nephrol., 30: 105–111, 1996); (Gittes, R. F. and R. M. Nakamura, Female urethral syndrome: A female prostatitis?, Western J. Medicine, 164: 435–438, 1996); (Miller, M. D. and J. M. Marshall, Uterine Response to Nerve Stimulation: Relation to Hormonal Status and Catecholamines, Am. J. Physiol., 209: 859–863, 1965); (Miller and Marshall, Uterine Response to Nerve Stimulation: Relation to Hormonal Status and Catecholamines, Am. J. Physiol., 209: 859–863, 1965); and (Hoffman, B. B., T. N. Lavin, R. J. Lefkowitz and R. R. Ruffolo, Jr., Alpha -Adrenergic Receptor Subtypes in Rabbit Uterus: Mediation of Myometrial Contraction and Regulation by Estrogens, J. Pharmacol. Exp. Ther., 219: 290–295, 1981, and Roberts, J. M., P. A. Insel and A. Goldfein, Regulation of Myometrial Adrenoreceptors and Adrenergic Response by Sex Steroids, Mol. Pharmacol., 20: 52–58, 1981).

Aqueous liquid compositions of the present invention are particularly useful for the treatment and prevention of benign prostatic hyperplasia, bladder outlet obstruction, neurogenic bladder, and uterine smooth muscle contraction.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the present invention means a sufficient amount of the compound to treat disorders, at a reasonable benefit/risk ratio applicable to any medical treatment., It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 30 mg/kg/day. For purposes of oral administration, more preferable doses can be in the range of from about 0.01 to about 10 mg/kg/day. If desired, the effective daily dose can be divided into multiple doses for purposes of administration, e.g. two to four separate doses per day.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, and choline. Cations may be interchanged by methods known in the art, such as ion exchange. Where compounds of the present invention are prepared in the carboxylic acid form, addition of a base (such as a hydroxide or a free amine) will yield the appropriate cationic form.

The term "pharmaceutically acceptable salt, ester, amide, and prodrug," as used herein, refers to carboxylate salts, amino acid addition salts, zwitterions, esters, amides, and prodrugs of compounds of formula I–VII which are within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the present invention include phosphate, tris and acetate.

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$- to -$C_6$ alkyl esters and $C_5$- to -$C_7$ cycloalkyl esters, although $C_1$- to -$C_4$ alkyl esters are preferred. Esters of the compounds of formula I–VII may be prepared according to conventional methods.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and Cl-to-$C_2$ dialkyl secondary amides are preferred. Amides of the compounds of formula I–VII may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems,* V. 14 of the A.C.S. Symposium Series, and in Edward B. Roche, ed., *Bioreversible Carriers in Drug Design,* American Pharmaceutical Association and Pergamon Press (1987), hereby incorporated by reference.

The term "prodrug ester group," as used herein refers, to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book "Pro-drugs as Novel Delivery Systems," by Higuchi and Stella, cited above.

The present invention contemplates pharmaceutically active metabolites formed by in vivo biotransformation of compounds of formula I–VII. The term pharmaceutically active metabolite, as used herein, refers to a compound formed by the in vivo biotransformation of compounds of formula I–VII. The present invention contemplates compounds of formula I–VII and metabolites thereof. A thorough discussion of biotransformation is provided in (Goodman and Gilman's, The Pharmacological Basis of Therapeutics, seventh edition).

What is claimed is:

1. A compound having the formula I

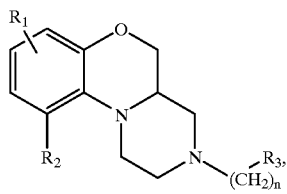

or a pharmaceutically acceptable salt thereof, wherein n is an integer 2–4;

$R_1$ and $R_2$ are independently selected from the group consisting of hydrogen, alkenyl, alkoxy, alkoxyalkyl, alkoxycarbonyl, alkyl, alkynyl, amino, aminoalkyl, carboxy, carboxyalkyl, halogen, hydroxy, hydroxyalkyl, and nitro; and $R_3$ is selected from the group consisting of

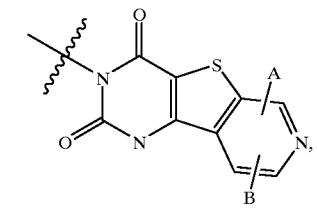

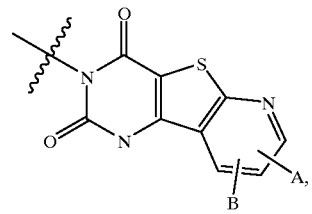

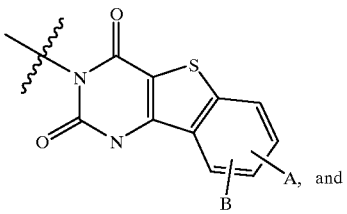

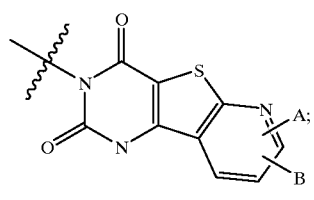

wherein A and B are independently selected from the group consisting of alkoxy, alkoxycarbonyl, alkyl, carboxy, cyano, halogen, hydroxyalkyl, nitro, and phenyl.

2. A compound according to claim 1 of formula II

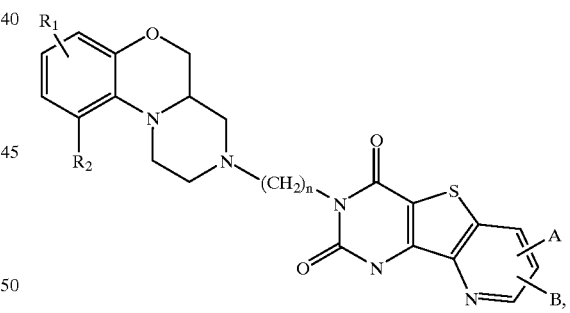

or a pharmaceutically acceptable salt thereof.

3. A compound according to claim 2 that is selected from the group consisting of (+) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(−) 3-[3-(1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(+) 3-[4-(1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(−) 3-[4-(1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(−) 3-[2-(10-methoxy-1,2,4a,5-tetrahydropyrazino[2,1-c][1,4]benzoxazin-3(4H)-yl)ethyl]pyrido[2',3':4,5]thieno[3,2-d]pyrimidine-2,4(1H,3H)-dione;

(−) 3-[3-(10-methoxy-1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]pyrido[2',3':4,5]thieno[3,2-d]pyrimidine-2,4(1H,3H)-dione;

(+) 3-[4-(10-methoxy-1,2,4a,5-tetrahydropyrazino[2,1-c][1,4]benzoxazin-3(4H)-(yl)butyl]pyrido[2',3':4,5]thieno[3,2-d]pyrimidine-2,4(1H,3H)-dione;

(+) 3-[2-(10-methoxy-1,2,4a,5-tetrahydropyrazino[2,1-c][1,4]benzoxazin-3(4H)-yl)ethyl]pyrido[2',3':4,5]thieno[3,2-d]pyrimidine-2,4(1H,3H)-dione; and (+) 3-[3-(10-methoxy-1,2,4a,5-tetrahydropyrazino[2,1-c][1,4]benzoxazin-3(4H)-yl)propyl]pyrido[2',3':4,5]thieno[3,2-d]pyrimidine-2,4(1H,3H)-dione.

4. A compound according to claim 1 of formula III

III or a pharmaceutically acceptable salt thereof.

5. A compound according to claim 4 that is selected from the group consisting of (+) 3-[2-(10-methoxy-1,2,4a,5-tetrahydropyrazino[2,1-c][1,4]benzoxazin-3(4H-yl)ethyl]-8-chloropyrazino[2',3':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]-8-chloropyrazino[2',3':4,5]thieno[3,2-d]pyrimidine-2,4(1H,3H)-dione; and (−) 3-[2-(10-methoxy-1,2,4a,5-tetrahydropyrazino[2,1-c][1,4]benzoxazin-3(4H)-yl)ethyl]-8-chloropyrazino[2',3':4,5]thieno[3,2-d]pyrimidine-2,4(1H,3H)-dione.

6. A compound according to claim 1 of formula IV

IV or a pharmaceutically acceptable salt thereof.

7. A compound according to claim 6 that is selected from the group consisting of (+) 3-[4-(1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(−) 3-[4-(1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione;

(−) 3-[4-(10-methoxy-1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione; and (+) 3-[4-(10-methoxy-1,2,4a,5-tetrahydropyrazino[2,1-c][1,4]benzoxazin-3(4H)-yl)butyl]pyrido[3',2':4,5]thieno[3,2-d]pyrimidine-2,4(1H,3H)-dione.

8. A compound according to claim 1 of formula V

V or a pharmaceutically acceptable salt thereof.

9. A compound according to claim 1 of formula VI

VI or a pharmaceutically acceptable salt thereof.

10. A compound according to claim 1 of formula VII

VII or a pharmaceutically acceptable salt thereof.

11. A method of treating benign prostatic hyperplasia in a host mammal in need of such treatment comprising administering a therapeutically effective amount of a compound of formula I.

12. A method of treating bladder outlet obstruction in a host mammal in need of such treatment comprising administering a therapeutically effective amount of a compound of formula I.

13. A method of treating neurogenic bladder in a host mammal in need of such treatment comprising administering a therapeutically effective amount of a compound of formula.

* * * * *

UNITED STATES PATENT AND TRADEMARK OFFICE
CERTIFICATE OF CORRECTION

PATENT NO.    : 6,376,488 B1                                              Page 1 of 1
DATED         : April 23, 2002
INVENTOR(S)   : Fatima Z Basha et al.

It is certified that error appears in the above-identified patent and that said Letters Patent is hereby corrected as shown below:

Column 34,
Lines 25-33, replace " 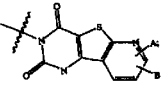 " with " 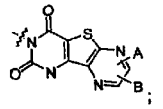 "

Column 36,
Line 64, replace "compound of formula." with -- compound of formula I. --

Signed and Sealed this

Fifth Day of November, 2002

Attest:

*Attesting Officer*

JAMES E. ROGAN
*Director of the United States Patent and Trademark Office*